(12) United States Patent
Han et al.

(10) Patent No.: US 10,253,309 B2
(45) Date of Patent: Apr. 9, 2019

(54) APPARATUS FOR SEPARATING FINE PARTICLES USING MAGNETOPHORESIS, AND METHOD FOR SEPARATING FINE PARTICLES USING SAME

(75) Inventors: Ki Ho Han, Gimhae-si (KR); Hwan Yong Lee, Gimhae-si (KR); Song I Han, Busan (KR); Seon Young Kim, Busan (KR); In Hak Choi, Busan (KR)

(73) Assignee: INJE UNIVERSITY INDUSTRY-ACADEMIC COOPERATION FOUNDATION, Gimhae-si, Gyeongsangnam-Do (KR)

( * ) Notice: Subject to any disclaimer, the term of this patent is extended or adjusted under 35 U.S.C. 154(b) by 1430 days.

(21) Appl. No.: 13/821,477

(22) PCT Filed: Aug. 19, 2011

(86) PCT No.: PCT/KR2011/006105
§ 371 (c)(1),
(2), (4) Date: Apr. 1, 2013

(87) PCT Pub. No.: WO2012/033291
PCT Pub. Date: Mar. 15, 2012

(65) Prior Publication Data
US 2013/0189755 A1    Jul. 25, 2013

(30) Foreign Application Priority Data

Sep. 10, 2010 (KR) .................. 10-2010-0088957
Jun. 13, 2011 (KR) .................. 10-2011-0057095

(51) Int. Cl.
*C12N 13/00* (2006.01)
*C07H 1/08* (2006.01)
(Continued)

(52) U.S. Cl.
CPC .......... *C12N 13/00* (2013.01); *B03C 1/0335* (2013.01); *B03C 1/32* (2013.01); *C07H 1/08* (2013.01);
(Continued)

(58) Field of Classification Search
CPC ..... B03C 1/0335; B03C 1/32; B03C 2201/18; G01N 27/745
See application file for complete search history.

(56) References Cited

U.S. PATENT DOCUMENTS 8,878,638 B2 * 11/2014 Bertacco ............... B03C 1/32
                                                 335/284
2003/0044832 A1    3/2003  Blankenstein
2008/0124779 A1 *  5/2008  Oh ............... B01L 3/502761
                                                 435/173.9

FOREIGN PATENT DOCUMENTS

KR    100787234 B1    12/2007
KR    100907213 B1    7/2009
(Continued)

OTHER PUBLICATIONS

Fulcrand et al., J. Micromech. Microeng. 19 (2009) 105019, 12 pages.*

(Continued)

*Primary Examiner* — Bobby Ramdhanie
*Assistant Examiner* — Denise R Anderson
(74) *Attorney, Agent, or Firm* — Lucas & Mercanti, LLP

(57) ABSTRACT

The present invention relates to an apparatus for separating fine particles using magnetophoresis, and to a method for separating fine particles using same, and particularly, to an apparatus for separating fine particles using magnetophoresis, which includes a fine, patterned magnetic structure capable of quickly and efficiently separating even particles (Continued)

that are weakly magnetized and coupled to fine particles, and to a method for separating fine particles using same.

10 Claims, 21 Drawing Sheets

(51) Int. Cl.
 *B03C 1/033* (2006.01)
 *B03C 1/32* (2006.01)
 *G01N 27/74* (2006.01)
 *G01N 15/10* (2006.01)

(52) U.S. Cl.
 CPC ........ *G01N 27/745* (2013.01); *B03C 2201/18* (2013.01); *B03C 2201/26* (2013.01); *G01N 15/1056* (2013.01)

(56) References Cited

FOREIGN PATENT DOCUMENTS

| KR | 20100079045 A | | 7/2010 | |
|----|----|----|----|----|
| WO | WO2010091874 | * | 8/2010 | ............... B03C 1/32 |

OTHER PUBLICATIONS

International Search Report of PCT/KR2011/006105 dated Apr. 23, 2012.
Supplementary European Search Report of EP11823724 completed Aug. 22, 2013.

* cited by examiner

Line 1: Size Marker
Line 2: Negative Control w/o RNA
Line 3: Purified Sample

APPARATUS FOR SEPARATING FINE PARTICLES USING MAGNETOPHORESIS, AND METHOD FOR SEPARATING FINE PARTICLES USING SAME

CROSS-REFERENCE TO RELATED APPLICATIONS

This application is a 371 of PCT/KR2011/006105 filed on Aug. 19, 2011, which claims the benefit of Korean Patent Application Nos. 10-2010-0088957 filed on Sep. 10, 2010 and 10-2011-0057095 filed on Jun. 13, 2011, the entire contents of each of which are incorporated herein by reference.

FIELD OF THE INVENTION

The present invention relates to an apparatus for separating fine particles using magnetophoresis and a method for separating fine particles using the same.

BACKGROUND OF THE INVENTION

Separation of cell type or components in the cells is required as the final purpose of a preparative tool for another analysis in diagnosis and treatment of the medical field and the research field. Now, there are many methods for classifying various kinds of cell types or components in the cells used in study rooms and clinical laboratories. A step of rapidly separating other kinds of particles, for example, virus, bacteria, cells and multicellular organism, is an essential step in various applicable fields of medical research, clinical diagnosis and environment analysis. Rapidly growing knowledge in a drug development and protein research allow researchers to quickly obtain many understanding about protein-protein interaction, cellular signal pathway and markers of metabolic processes. This information is difficult or impossible to be obtained by using a single protein detecting method, for example a traditional method such as ELISA or western blotting. Accordingly, the separation of cell type or components in the cells is much more required.

As the method for separating a certain target biomolecules from a biological sample such as blood plasma, methods using silica, glass fibers, anionic ion exchange resins or magnetic beads are known. Among them, according to the method using the magnetic beads, the target biomolecules is extracted: by inserting the magnetic beads having probes, which can be combined with the target biomolecules, on the surface into a sample solution to capture the target biomolecules, and then by separating the magnetic beads from the sample solution. The method for separating the target biomolecules by using the magnetic beads (bead based separation) was already commercialized, and broadly used for separating cells, proteins, nucleic acids or other biomolecules. For example, U.S. Pat. No. 6,893,881 discloses a method for separating a certain target cells by using paramagnetic beads coated with an antibody.

The magnetophoresis separation technology using a high gradient magnetic field (HGMS: high gradient magnetic separation) for separating the magnetic beads has been steadily studied for a long time due to its advantages of simple structure, high efficiency, easy used and no hydrolysis compared with dielectrophoresis. Another advantage of the magnetophoresis is that biological characteristics can be maintained by biocompatible bonds between the magnetic particles and bio analyte, and the force of the magnetophoresis is not affected by media.

The existing magnetophoresis method employs a magnetic energy source, which applies a magnetic field to separate a magnetic sample to be separated by magnetophoresis, and a magnetic material microstructure domain, which amplifies the gradient of the magnetic field applied by the external magnetic energy source; and separates the magnetic sample to be separated according to the gradient of the magnetic field by applying the magnetic field from the magnetic energy source. As one example, as shown in FIG. 1, Korean Patent Registration No. 10-0791036 discloses a method for separating pure carbon nano tubes by arranging a ferromagnetic material structure 40 besides a microfluidic channel 30, and by applying external magnetic field to the direction perpendicular to the flow of the carbon nanotube sample.

However, it was difficult to induce enough magnetic force for the fine particles with the gradient magnetic field generated from the apparatus used for the existing magnetophoresis method, and therefore, the efficiency for separating the fine particles was low and the time for separation was long. Accordingly, there was a problem that it is difficult to use the fine particles to be separated for separating and extracting from a sample.

SUMMARY OF THE INVENTION

In order to solve the problems of the existing magnetophoresis apparatuses, the present invention is objected to provide an apparatus for separating fine particles using magnetophoresis, which is capable of quickly separating with excellent efficiency even when the fine particles to be separated are weakly magnetized, by containing a patterned fine structure of a magnetic material, and a method for separating the fine particles using the same.

In order to accomplish one object of the present invention, the present invention provides an apparatus for separating fine particles using magnetophoresis comprising:

an upper substrate;

a lower substrate comprising a patterned fine structure of a magnetic material;

a microfluidic channel, which is formed between the upper substrate and the lower substrate, and where a sample comprising fine particles passes; and an external magnetic field source generating a magnetic field around the patterned fine structure of a magnetic material.

The present invention is characterized that the microfluidic channel is divided into: a microfluidic channel domain for injection comprising a plurality of inlets, where a sample comprising fine particles and a buffer are injected; a microfluidic channel domain for separation, where the fine particles contained in the injected sample are separated by magnetophoresis while passing through; and a microfluidic channel domain for discharge comprising a plurality of outlets, where the fine particles separated while passing through the microfluidic channel domain for separation and the rest of the sample are separately discharged, respectively.

The present invention is characterized that the inlet of the microfluidic channel domain for injection comprises a sample inlet and a buffer inlet.

The present invention is characterized that the microfluidic channel domain for discharge is consisting of an outlet connected to a chamber collecting the fine particles in the sample, and an outlet connected to a chamber collecting the rest of the sample; and the outlet connected to a chamber collecting the fine particles and the outlet connected to a chamber collecting the rest of the sample are separated.

The present invention is characterized that the fine structure of a magnetic material is a plurality of linear structures, and is contained in the lower substrate by being patterned thereon to have a certain angle of inclination to the direction of sample flow at the microfluidic channel domain for separation.

The present invention is characterized that, when the angle of inclination to the direction of sample flow is θ, the fine structure of a magnetic material is contained in the lower substrate by being patterned to make the θ change at the microfluidic channel domain for separation.

The present invention is characterized that, when the angles of inclination of the fine structure of a magnetic material to the direction of sample flow, θ, from the microfluidic channel for sample injection to the microfluidic channel domain for discharge are θ1, θ2, θ3 . . . θn in order, respectively, the θ1, θ2, θ3 . . . θn satisfy the following relation expression:

$$\theta 1 \leq \theta 2 \leq \theta 3 \leq \ldots \leq \theta n \leq 90 (3 \leq n).$$

The present invention is characterized that the θn is 90°.

The present invention is characterized that the microfluidic channel domain for injection comprises a buffer inlet, and a plurality of sample inlets symmetrically formed on both sides of the buffer inlet.

The present invention is characterized that the microfluidic channel domain for injection comprises a sample inlet, and a plurality of buffer inlets symmetrically formed on both sides of the sample inlet.

The present invention is characterized that the fine structure of a magnetic material is patterned and contained on the lower substrate to make both sides have symmetry based on the center of the microfluidic channel for separation.

The present invention is characterized that, when the angles of inclination of the fine structure of a magnetic material to the direction of sample flow θ from the microfluidic channel for sample injection to the center of the microfluidic channel for separation are θ1, θ2, θ3 . . . θn in order, respectively, the θ1, θ2, θ3 . . . θn satisfy the following relation expression:

$$\theta 1 \leq \theta 2 \leq \theta 3 \leq \ldots \leq \theta n \leq 90 \ (3 \leq n)$$

The present invention is characterized that the θn is being 90°.

The present invention is characterized that a point, where the angle of inclination of the fine structure of a magnetic material to the direction of sample flow θ is changed from θn−1 to θn, is located in a horizontally extended part of the outlet connected to a chamber, where the fine particles in the sample are collected.

The present invention is characterized that the fine structure of a magnetic material is patterned and contained on the lower glass substrate by molding.

The present invention is characterized that the fine structure of a magnetic material is composed of a ferromagnetic material or a ferromagnetic alloy.

The present invention is characterized that the fine structure of a magnetic material comprises a nickel-iron alloy or a nickel-iron-cobalt alloy.

The present invention is characterized that the fine structure of a magnetic material is any one of permalloy (Fe 50%, Ni 50%), moly permalloy (Ni 81%, Fe 17%, Mo 2%) or superalloy (Co 52%, Fe 26%, Ci 22%).

The present invention is characterized that the substrate is made with a material selected from glass, silicone, polycarbonate, quartz, polymethylmethacrylate, acryl, polyolefin, or any combination thereof.

The present invention is characterized that in the apparatus for separating fine particles using magnetophoresis, the angle of inclination of the fine structure of a magnetic material to the direction of sample flow, the thickness of the fine structure of a magnetic material, gap between the plurality of the fine structures of the magnetic material, the number of the structures to be installed, the size of the external magnetic field source and the fluid flow rate in the microfluidic channel are changed according to the fine particles to be separated.

In the present invention, the apparatus for separating fine particles using magnetophoresis is characterized that the upper substrate comprises a patterned fine structure of a magnetic material, and the patterned fine structure of a magnetic material of the upper substrate is patterned to the same shape as the lower substrate.

Further, as a method for separating the fine particles using the apparatus for separating fine particles according to the present invention, the present invention provides a method for separating the fine particles, which is characterized by comprising: a first step of injecting a sample comprising magnetic fine particles into a sample inlet of a microfluidic channel domain for injection; a second step of injecting a buffer into a buffer inlet; a third step of separating the fine particles, wherein an external magnetic field source is generated, thereby a magnetic force is generated around a patterned fine structure of a magnetic material, and the fine particles are separated by the magnetic force generated around the patterned fine structure of a magnetic material while the sample comprising the fine particles is passing through a microfluidic channel for separation; and a fourth step of collecting the fine particles combined with the magnetic particles separated in the third step at the microfluidic channel domain for discharge.

Hereinafter, the apparatus for separating fine particles using magnetophoresis of the present invention and a method for separating fine particles will be described in detail with reference to the accompanying drawings.

A cross-sectional view and a plane view of the apparatus for separating fine particles using magnetophoresis according to one embodiment of the present invention are illustrated in FIG. 2 and FIG. 3.

As shown in FIG. 2, the apparatus for separating fine particles using magnetophoresis according to one embodiment of the present invention is composed of: an upper substrate 100; a lower substrate 300 comprising a patterned fine structure of a magnetic material 200; and a microfluidic channel 400, which is formed between the upper glass substrate and the lower glass substrate, and where a sample containing fine particles passes.

Further, as shown in FIG. 3, the microfluidic channel 400 is composed of sequentially connected: a microfluidic channel domain for injection 410 comprising a plurality of inlets, where a sample comprising the fine particles and a buffer are injected; a microfluidic channel domain for separation 420, where the fine particles contained in the injected sample are separated by magnetophoresis while passing through; and a plurality of microfluidic channel domains for discharge 430, where the separated fine particles are discharged.

The plurality of inlets of the microfluidic channel for injection 410 is formed to a sample inlet 440 and a buffer inlet 450, and the microfluidic channel domain for discharge is composed of an outlet 460 connected to a chamber collecting the fine particles, and a plurality of outlets 470 connected to chambers collecting the rest of the sample, and the plurality of outlets are separately contained.

In the present invention, the fine structure of a magnetic material is one or a plurality of linear structures, and is contained in the lower substrate by being patterned thereon to have a certain angle of inclination to the direction of sample flow at the microfluidic channel domain for separation.

In the present invention, the fine structure of a magnetic material is characterized by being patterned on the lower substrate. In the present invention, the fine structure of a magnetic material is contained inside the lower substrate by being patterned by a molding method. Accordingly, the fine structure of a magnetic material does not directly contact to the sample but also a magnetic force can be directly transferred to the fine particles formed around the fine structure of a magnetic material.

A process for patterning one or a plurality of fine structures of a magnetic material in the form of a linear structure on the lower glass substrate by molding is illustrated in FIG. 4.

The fine structure of a magnetic material of the lower glass substrate is patterned on the lower glass substrate by i) seed layer deposition process, ii) a process for forming a pattern of the fine structure of a magnetic material by photoresist, iii) a process for depositing the fine structure of a magnetic material according to the formed pattern, and iv) a process for forming a coated layer by evenly coating an epoxy resin all over the lower glass substrate comprising the fine structure of a magnetic material.

When describing this in detail, the seed layer is deposited on the bottom glass substrate, and the pattern for depositing the ferromagnetic nickel wire as the fine structure of a magnetic material by coating the photoresist is formed.

In the present invention, the fine structure of a magnetic material is in the form of a plurality of linear structures, and it can be formed in the form of a ferromagnetic wire having a certain thickness, and direction and continuity, but not limited thereto. The ferromagnetic nickel wire is deposited according to the formed pattern, and then the photoresist is removed (A of FIG. 4). After removing the photoresist, the lower glass substrate containing the fine structure of a magnetic material is manufactured by coating an epoxy adhesive as a adhesion mean on the surface, curing at 85° C. for 6 hours so as to coat the epoxy resin on the surface of the fine structure of a magnetic material (B of FIG. 4). Then, a chromium layer of 1000 Å is deposited on the upper glass substrate so as to increase adhesion between the SU-8 2050 and the glass substrate, and SU-8 2050 photoresist is spin coated thereon to form a pattern of the microfluidic channel, and then the sample inlet and the outlet part are prepared on the upper glass substrate by using a drill (C of FIG. 4). Then, an adhesive for UV curing, 1187-M is coated on the laminated upper glass substrate and the lower glass substrate followed by irradiating UV so as to combine the upper glass substrate and the lower glass substrate (D of FIG. 4), and then the sample inlet and the buffer inlet are manufactured on the upper glass substrate by using a O-ring.

In the present invention, in the microfluidic channel domain for sample injection 410, a sample containing the fine particles and a buffer are injected through the sample inlet 440 and the buffer inlet 450, respectively. The fine particles, which can be separated by the apparatus for separating fine particles using magnetophoresis according to the present invention, may be any fine particles, which can combine with magnetic particles, such as DNA, antibodies, peptides, small peptides and the like, and it may be preferably RNA or circulating tumor cells (CTC).

A method for combining the fine particles and the magnetic particles for separation using the apparatus for separating fine particles using magnetophoresis according to the present invention is not particularly limited, and any method, generally known in the art, for each of the fine particles can be used for manufacture. Namely, it is preferred that the magnetic particles is an oxide of one or more selected from the group consisting of cobalt, iron, manganese, zinc, nickel and copper, but any material showing magnetic property can be used without limitation. The surfaces of these magnetic particles are modified followed by reacting with the fine particles to be separated, so as to fix the fine particles on the surfaces of the magnetic particles.

Hereinafter, a principle of the apparatus for separating fine particles using magnetophoresis of the present invention will be described.

The direction and the magnetic force of the magnetic field applied to the fine particles, which are located in the microfluidic channel of the apparatus for separating fine particles using magnetophoresis of the present invention are illustrated in FIG. and FIG. 6.

In the present invention, the ferromagnetic wire as the fine structure of a magnetic material is manufactured and contained in the substrate to having the angle to the direction of sample flow of θ through a printed circuit process. And the fine particles combined with the magnetic particles, which are inserted through the sample inlet of this separating apparatus, pass over the fine structure of a magnetic material contained in the lower substrate with an acute angle (θ<90°). At this time, when the external magnetic field source is applied, as shown in FIG. 5, a high gradient magnetic field is formed around the ferromagnetic wire as the fine structure of a magnetic material, contained in the lower substrate, and therefore, the fine particles combined with the magnetic particles, which are placed around the wire as the fine structure of a magnetic material, receive magnetic force Fm to the direction of the fine structure of a magnetic material under the influence of the high gradient magnetic field. Accordingly, the fine particles combined with the magnetic particles receive force to the lateral direction of the fine structure of a magnetic material by a drag force of the fluid and the magnetic force and then move. Namely, when the magnetic force does not work, as shown in FIG. 6, the particles horizontally move to the injection direction because only the drag force of the fluid affects to both of the magnetic fine particles and the non-magnetic fine particles, but when the magnetic force works, the fine particles under the influence of the magnetic force receive the force to the lateral direction of the fine structure of a magnetic material, and the route is changed, thereby being separated from the non-magnetic particles.

The drag force (Fd) of the fluid working on the fine particles combined with the magnetic particles, and the magnetic force (Fm) working on the lateral direction by the magnetic force of fine structure of a magnetic material are illustrated in FIG. 6. In FIG. 6, the force Fmx working on the fine particles combined with the magnetic particles to the x-axis direction can be expressed as the following formula.

$$F_{mx} = \quad (1)$$

$$-\frac{2V_P M_{PS} x k a^2 B_0}{(x^2-z^2)^2 \sqrt{(x^2-z^2)^2 - 2ka^2(x^2-z^2) + k^2 a^4}}(x^2 - 3z^2 - ka^2)$$

$$k = \frac{\mu_W - \mu_B}{\mu_W + \mu_B}$$

(wherein, Vp=volume of the magnetic bead,
Mps=saturation magnetization of the beads,
$\mu_B$=permeability of the buffer solution
$\mu_W$=permeability of the ferromagnetic wire
a=the effective radius of the ferromagnetic wire
$B_0$=applied external magnetic flux
x, z=axes of a Cartesian coordinate)

Accordingly, the total force working on the fine particle, which is expressed as a vector sum of the drag force (Fd) of the fluid and the magnetic force (Fm), can be expressed as follows.

$$\overline{F}_1 = \overline{F}_{mx} + \overline{F}_d = (F_{mx} + F_d \sin\theta)\overline{a}_x - F_d \cos\theta\overline{a}_y, \quad (2)$$

(wherein, $F_d$ is the drag force of the fluid working on the fine particles combined with the magnetic particles, i.e., the hydrodynamic drag force on a magnetic bead)

In the above formula, the lateral velocity of the fine particles combined with the magnetic particles can be expressed as follows.

$$\overline{v}_l = \frac{\overline{F}_l}{6\pi \eta d} = \beta[(F_{mx} + F_d \sin\theta)\overline{a}_x - F_d \cos\theta\overline{a}_y], \quad (3)$$

$$\beta = \frac{1}{6\pi \eta d}$$

When the z is fixed, the distance to the x-axis direction and the y-axis direction are as follows.

$$dx = \beta(F_{mx} + F_d \sin\theta)dt$$

$$y = -\mu F_d \cos\theta t. \quad (4)$$

The travel distance of the magnetic particles to the y'-axis can be expressed as follows.

$$\Delta y' = x \cos\theta + y \sin\theta. \quad (5)$$

From the above formulae, it can be found that the travel distance of the magnetic particles to the horizontal direction dx and the travel distance to the lateral direction Δy' increase when the magnetic force $F_{mx}$ to the x-axis direction increases or the angle of inclination θ between the sample flow and the magnetic wire increases.

The magnetic forces received in the magnetic field of the fine particles and the rest of the sample, which are injected into the microfluidic channel domain for injection through the sample inlet 440, become different from each other, and the travel distances to the x-axis direction and the y-axis direction by these magnetic forces become different. Consequently, after passing through the channel, the fine particles are collected in a chamber for discharging the fine particles 470 through the fine particles outlet, and the rest of the sample except the fine particles are discharged to the other microfluidic channel domain for discharge 460.

It is preferred that the angle of inclination to the direction of sample flow θ formed by the ferromagnetic wire as the fine structure of a magnetic material is decided in a range of more than 0° to less than 90° because, when the θ value is excessively small or large, the efficiency for separating the fine particles combined with the magnetic particles may be reduced. When the θ value becomes 90° or more, $F_{mx} + F_d \sin\theta < 0$ in the above formula (4), and in this case, the fine particles combined with the magnetic particles can't pass the ferromagnetic wire patterned on the lower substrate. Consequently, the travel distance to the lateral direction increases indefinitely. Namely, the fine particles are not collected to the chamber collecting the samples but diffused.

Further, in the present invention, in order to induce the particles, injected into the sample inlet 440, to the outlet 470 by path induction by the magnetic field from when the sample is injected into the sample inlet, as shown in FIG. 7, it is preferred that the fine structure of a magnetic material is sloped on the whole from the sample inlet to the direction of the buffer inlet to have an angle.

Further, the apparatus for separating fine particles using magnetophoresis according to the present invention is characterized that the angle of inclination of the fine structure of a magnetic material to the direction of sample flow is changed at the microfluidic channel domain for separation.

When the applied external magnetic field is strong, the strong magnetic field is formed to the ferromagnetic wire as the fine structure of a magnetic material, and therefore, the fine particles may not be discharged through the channel, and may be accumulated around the ferromagnetic wire. Accordingly, in the present invention, in order to make the fine particles pass through the microfluidic channel for separation and be smoothly discharged through the microfluidic channel for discharge, it is preferred that the fine structure of a magnetic material is contained in the lower substrate by being patterned to make the angle of inclination θ change at the microfluidic channel domain for separation.

A mimetic diagram of the case that the angle of inclination to the direction of sample flow θ of the fine structure of a magnetic material, manufactured according to one embodiment of the present invention, is changed at the microfluidic channel domain for separation is illustrated in FIG. 7.

Further, as shown FIG. 7, in the present invention, when the angles of inclination of the fine structure of a magnetic material to the direction of sample flow, θ, from the microfluidic channel for sample injection to the microfluidic channel domain for discharge are θ1, θ2, θ3 ... θn in order, respectively, the θ1, θ2, θ3 ... θn is characterized by satisfying the following relation expression:

θ1≤θ2≤θ3≤ ... ≤θn≤90(3≤n).

Namely, in the present invention, the angle of inclination of the fine structure of a magnetic material to the direction of sample flow (θ) is changed three times or more (3≤n), and the path of the fine particles is gradually changed by gradually increasing the angle of inclination θ from the microfluidic channel for sample injection, where the sample is injected, to the microfluidic channel domain for discharge, where the sample is discharged Accordingly, the fine particles can be separated to the chamber for discharge with high efficiency by preventing agglomeration of the fine particles by the magnetic force around the fine structure of a magnetic material.

Further, as shown in FIG. 7, in the present invention, it is preferred that: the final angle of inclination θn of the angle of inclination of the fine structure of a magnetic material to the direction of sample flow is 90°; and the point P, where the angle of inclination of the fine structure of a magnetic material to the direction of sample flow θ is changed from θn−1 to θn, is located in the A domain marked in FIG. 7, i.e., a horizontally extended part of the outlet connected to the chamber 470, where the fine particles are collected.

When the fine structure of a magnetic material makes the angle of 90° to the direction of sample flow, the force working on the fine particles by the magnetic force becomes 0, thereby the fine particles receives only the force by the fluid flow. Accordingly, the high efficiency for separation can be obtained because all of the fine particles are separated along the fluid flow without being agglomerated around the fine structure of a magnetic material. Further, the magnetic force working on the fine particles from the point P, where the angle of inclination of the fine structure of a magnetic material to the direction of sample flow $\theta$ is changed from $\theta n-1$ to $\theta n$, becomes 0, and since then, only the force by the fluid flow to the horizontal direction works. Accordingly, it is preferred that the point P, where the angle of inclination of the fine structure of a magnetic material to the direction of sample flow $\theta$ is changed from $\theta n-1$ to $\theta n$, is located in the A domain marked in FIG. 7, i.e., a horizontally extended part of the outlet connected to the chamber, where the fine particles are collected, in order to improve the separation efficiency.

In the apparatus for separating fine particles using magnetophoresis according to another embodiment of the present invention, the microfluidic channel domain for injection can comprise a buffer inlet, and a plurality of sample inlets symmetrically formed on both sides of the buffer inlet; or a sample inlet, and a plurality of buffer inlets symmetrically formed on both sides of the sample inlet.

In the present invention, the case of comprising the buffer inlet 450 and the plurality of sample inlets 440 symmetrically formed on both sides of the buffer inlet, thereby comprising a plurality of outlets is mimetically illustrated in FIG. 8, and in the present invention, the case of comprising the sample inlet, and the plurality of buffer inlets symmetrically formed on both sides of the sample inlet, thereby comprising the plurality of outlets is mimetically illustrated in FIG. 9.

As shown in FIG. 8 and FIG. 9, when comprising the buffer inlet, and the plurality of sample inlets symmetrically formed on both sides of the buffer inlet; or a sample inlet, and a plurality of buffer inlets symmetrically formed on both sides of the sample inlet, it is preferred that the fine structure of a magnetic material is patterned to make both sides have symmetry based on the center line (C-C') of the microfluidic channel for separation.

Further, as shown in FIG. 8, it is preferred for particle separation that: when comprising the buffer inlet, and the plurality of sample inlets symmetrically formed on both sides of the buffer inlet, the outlet 460 for discharging the rest of the sample is designed to be both sides of the outlet 470, where the fine particles to be separated is separated; and as shown in FIG. 9, when comprising the sample inlet, and the plurality of buffer inlets symmetrically formed on both sides of the sample inlet, the outlet 470 for discharging the fine particles is designed to be both sides of the middle outlet 460, where the rest of the sample is discharged is separated.

Like the embodiments described above, in the embodiments shown in FIG. 8 and FIG. 9, the fine structure of a magnetic material is formed to be sloped from around the sample inlet to the direction of inducing to the outlet and the direction away from the buffer inlet. Further, it is formed while the angle of inclination of the fine structure of a magnetic material to the direction of sample flow $\theta$ is changed from the microfluidic channel for sample injection to the microfluidic channel domain for discharge, and when the angles of inclination of the fine structure of a magnetic material to the direction of sample flow $\theta$ from the microfluidic channel for sample injection to the microfluidic channel for discharge are $\theta 1, \theta 2, \theta 3 \ldots \theta n$ in order, respectively, the $\theta 1, \theta 2, \theta 3 \ldots \theta n$ is characterized by satisfying the following relation expression:

$$\theta 1 \leq \theta 2 \leq \theta 3 \leq \ldots \leq \theta n \leq 90 (3 \leq n).$$

Further, the point P, where the angle of inclination of the fine structure of a magnetic material to the direction of sample flow $\theta$ is changed from $\theta n-1$ to $\theta n$, is located in the A domain marked in FIG. 8 and FIG. 9, i.e., a horizontally extended part of the outlet connected to the chamber, where the fine particles are collected, in order to improve the separation efficiency.

In the present invention, as described above, it is preferred that the patterned fine structure of a magnetic material is one or a plurality of linear structures, and when it is the plurality of linear structures, as shown in FIGS. 7 to 9, all of the linear structures are formed in the same shape; and it is also possible to be contained in the forms of diversely changing the number, that the angle of inclination is changed, and the point, where the angle is changed, to each of the linear structure, for example, a part of them is formed to be changed two times in the angle of inclination, and the other part is formed to be changed three times in the angle of inclination.

In the present invention, the upper substrate can further comprise a patterned fine structure of a magnetic material.

The cases that the upper substrate according to one embodiment of the present invention comprises the patterned fine structure of a magnetic material are illustrated in FIG. 10 and FIG. 11. As shown in FIG. 10 and FIG. 11, the upper substrate 100 comprises the patterned fine structure of a magnetic material 500 in the same shape of the patterned fine structure of a magnetic material 200 of the lower substrate 300. When the both of the upper substrate and the lower substrate comprise the patterned fine structure of a magnetic material, the particles in the channel receives stronger magnetic force than the case of containing the fine structure only in the lower substrate, and higher separation efficiency can be obtained resulted by improving the problem of generation of lower magnetic force to the particles close to the upper substrate and far from the lower substrate.

In the present invention, the fine structure of a magnetic material is characterized by consisting of a ferromagnetic material or a ferromagnetic alloy. The fine structure of a magnetic material comprises a nickel-iron alloy or a nickel-iron-cobalt alloy, and specifically, it is preferred that the fine structure of a magnetic material is at least one of permalloy (Fe 50%, Ni 50%), moly permalloy (Ni 81%, Fe 17%, Mo 2%) or superalloy (Co 52%, Fe 26%, Ci 22%).

In the present invention, the substrate is not particularly limited, and it is preferred to be made with a material selected from glass, silicone, polycarbonate, quartz, polymethylmethacrylate, acryl, polyolefin, or any combination thereof.

In the apparatus for separating fine particles using magnetophoresis according to the present invention, the angle of inclination of the fine structure of a magnetic material to the direction of sample flow, the thickness of the fine structure of a magnetic material, gap between the plurality of the fine structures of the magnetic material, the number of the structures to be installed, the size of the external magnetic field source and the fluid flow rate in the microfluidic channel can be changed according to the fine particles to be separated.

Accordingly, in the present invention, the efficiency for separating the fine particles can be optimized by changing the conditions generating the magnetic force such as the angle of inclination of the ferromagnetic wire to the direction of sample flow, the thickness of the ferromagnetic wire patterned on the lower substrate, gap, the number of installation and the like.

Further, a method for separating fine particles using the apparatus for separating fine particles using magnetophoresis manufactured as described above comprises: the first step of injecting the sample comprising the fine particles combined with the magnetic particles into the sample inlet of the microfluidic channel domain for injection; the second step of injecting a buffer into a control fluid inlet; the third step of separating the fine particles combined with the magnetic particles from the rest of the materials by applying the external magnetic field, while the sample comprising the fine particles combined with the magnetic particles is passing through the microfluidic channel for separation; and the fourth step of collecting the fine particles combined with the magnetic particles separated in the third step at the microfluidic channel domain for discharge.

The third step of the method for separating fine particles of the present invention is characterized that the fine particles are separated by controlling the size of the external magnetic field source, which is connected to the fine structure of a magnetic material and forms the magnetic field, and the fluid flow rate in the microfluidic channel, so as to control the movement of the fine particles.

In the present invention, in order to analyze the characteristics of the fine particles separated as described above, extra operations such as PCR can be performed, and particularly, in the case of the CTC, conditions of patients and the like can be interpreted from the separated CTC.

Advantageous Effects of the Invention

The apparatus for separating the fine particles using magnetophoresis of the present invention has effects of: improving the magnetic force applied to the magnetic particles by comprising the fine structure of a magnetic material on the lower glass substrate by a molding process; and improving the efficiency for separating the fine particles combined with the magnetic particles and reducing the separation time by controlling the moving direction of the magnetic particles by patterning the fine structure of a magnetic material to have a certain angle of inclination of the direction of sample flow.

BRIEF DESCRIPTION OF DRAWINGS

The above and other objects and features of the present invention will become apparent from the following description of the invention taken in conjunction with the following accompanying drawings, which respectively show.

DETAILED DESCRIPTION OF THE INVENTION

Hereinafter, the present invention will be described in further detail with reference to examples. These examples are illustrative purposes only and are not to be construed to limit the scope of the present invention.

<Preparation Example 1> Preparation of Apparatus for Separating Fine Particles Combined with Magnetic Particles by Magnetophoresis In order to form a microfluidic channel, a Ti/Cu/Cr seed layer was deposited on a bottom glass substrate of 0.7 mm thick (Borofloat™, Howard Glass Co., Worchester, Mass.), a pattern was formed by photoresist, and then a ferromagnetic nickel wire of 30 μm thick was formed through a plating process.

In this Example, two ferromagnetic nickel wires were contained in the lower glass substrate of a microfluidic channel for separation part, and one wire of them was contained with an angle of inclination to the direction of sample flow of 5.7°, and the other wire was patterned, wherein the angle of inclination was 7.1° at first followed by being changed to 11.3° at the end of the microfluidic channel for separation, and then changed again to 90°.

In order to reduce the phenomenon that cells are attached to the surface of the microfluidic channel, the ferromagnetic nickel wire was constructed to be separated 100 μm from the channel surface of a microfluidic channel part for separation. A lower substrate comprising the ferromagnetic nickel wire as a magnetic structure was manufactured by removing the photoresist, coating an epoxy adhesive followed by leveling the surface.

Figure 1:
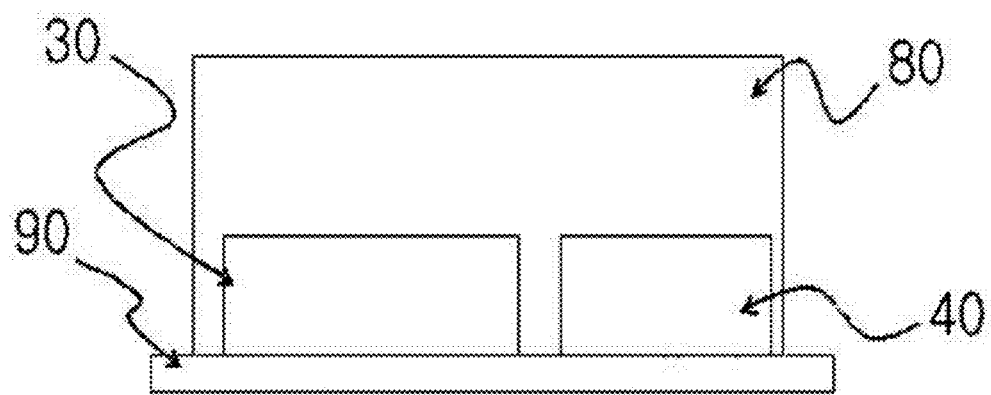
FIG. 1: a schematic diagram of the existing magnetophoresis apparatus.
Figure 2:
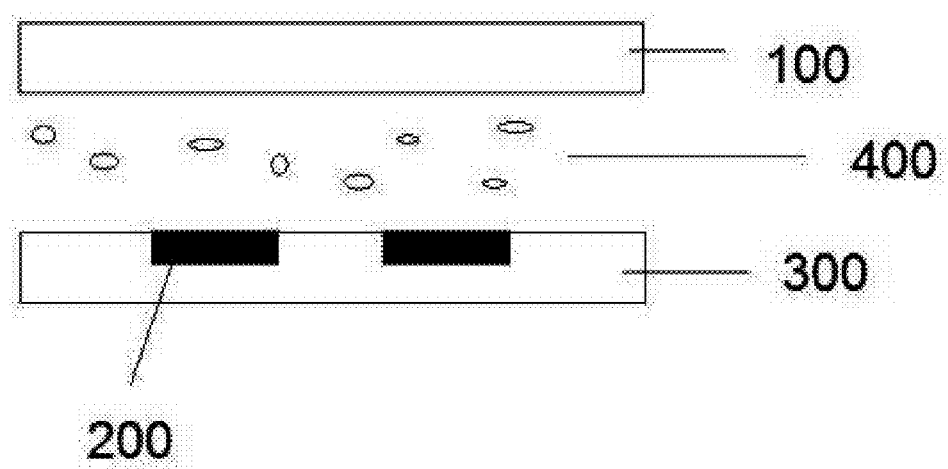
FIG. 2 and FIG. 3 are a cross-sectional view and a plane view of the apparatus for separating fine particles using magnetophoresis according to one embodiment of the present invention.
Figure 3:
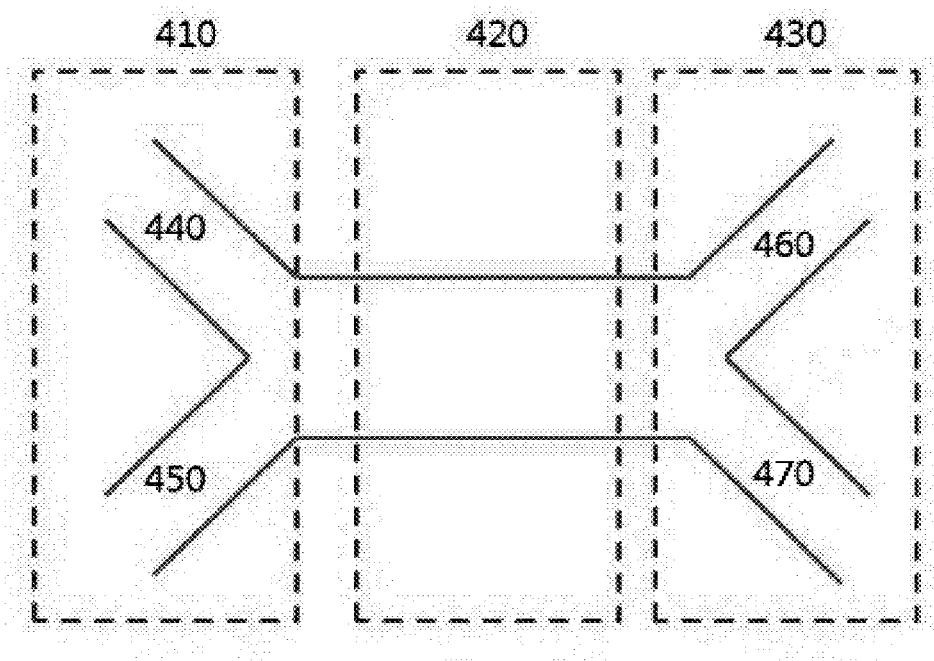
Figure 4:
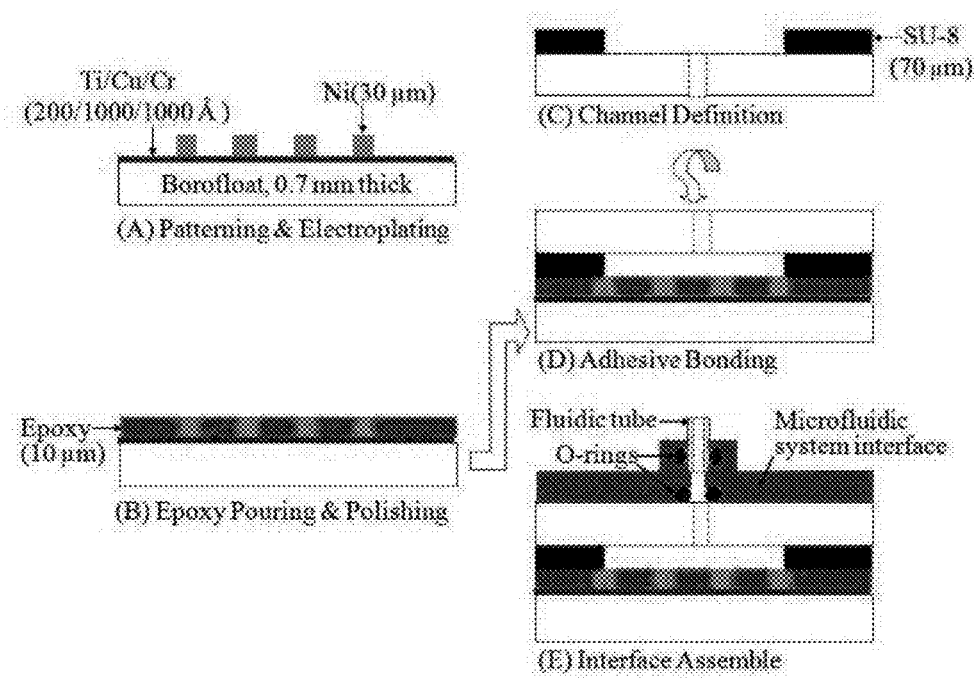
FIG. 4 is a drawing showing a process for manufacturing the fine structures of a magnetic material to be contained in the lower glass substrate by molding.
Figure 5:
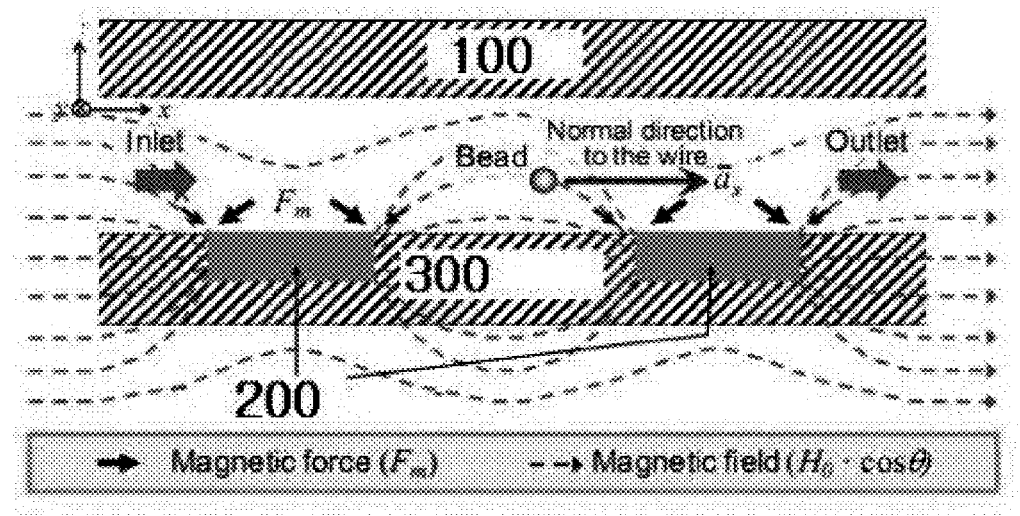
FIG. 5 and FIG. 6 are drawings showing the direction of the magnetic field and the magnetic force applied to the fine particles in the microfluidic channel when external magnetic field is applied to the apparatus for separating fine particles using magnetophoresis of the present invention.
Figure 6:
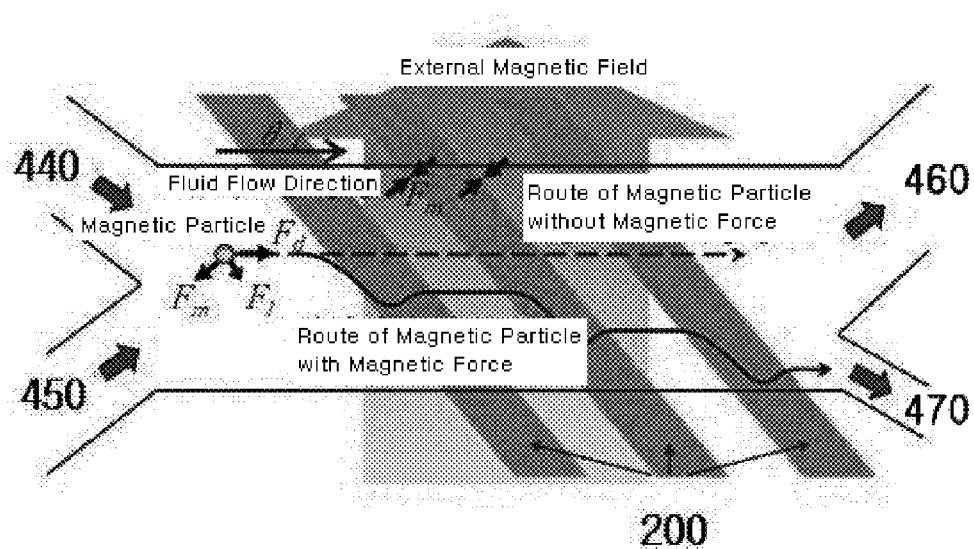
Figure 7:
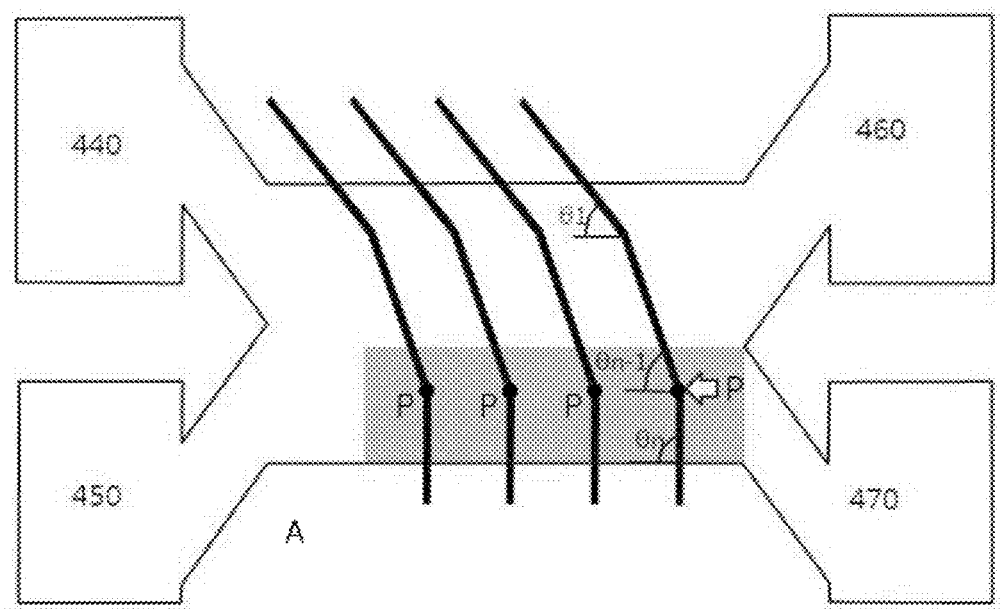
FIG. 7 is a mimetic diagram of the apparatus for separating fine particles using magnetophoresis of the present invention when the angle of inclination of the fine structure of a magnetic material is changed according to one embodiment of the present invention.
Figure 8:
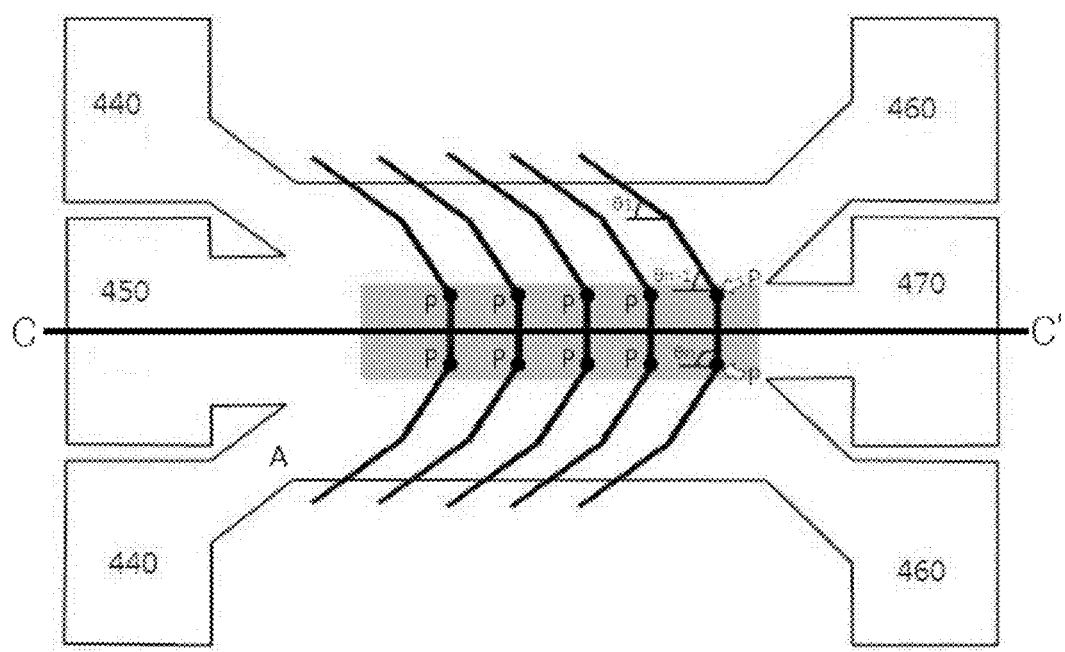
FIG. 8 and FIG. 9 are mimetic drawings showing the apparatus for separating fine particles using magnetophoresis according to another embodiment of the present invention.
Figure 9:
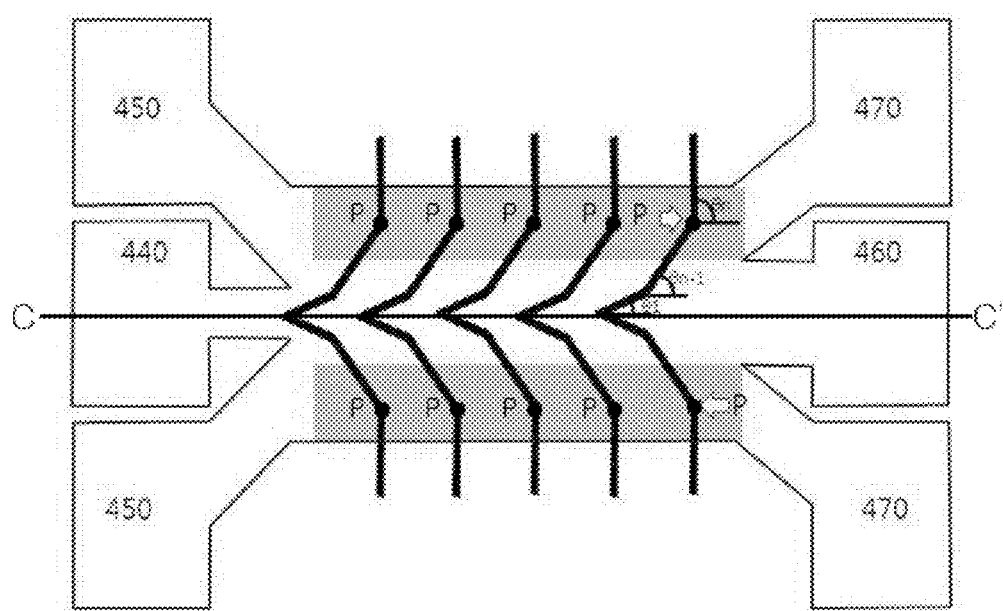
Figure 10:
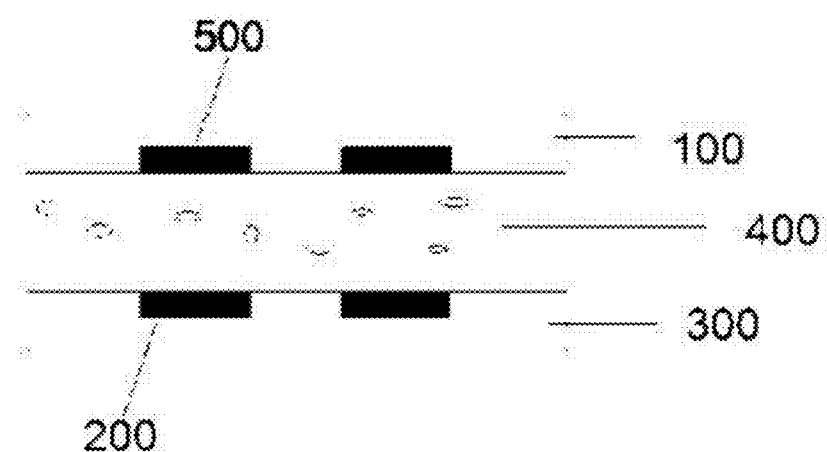
FIG. 10 is a mimetic drawing showing the apparatus for separating fine particles using magnetophoresis, which also contains the fine structure of a magnetic material in the upper substrate, according to another embodiment of the present invention.
Figure 11:
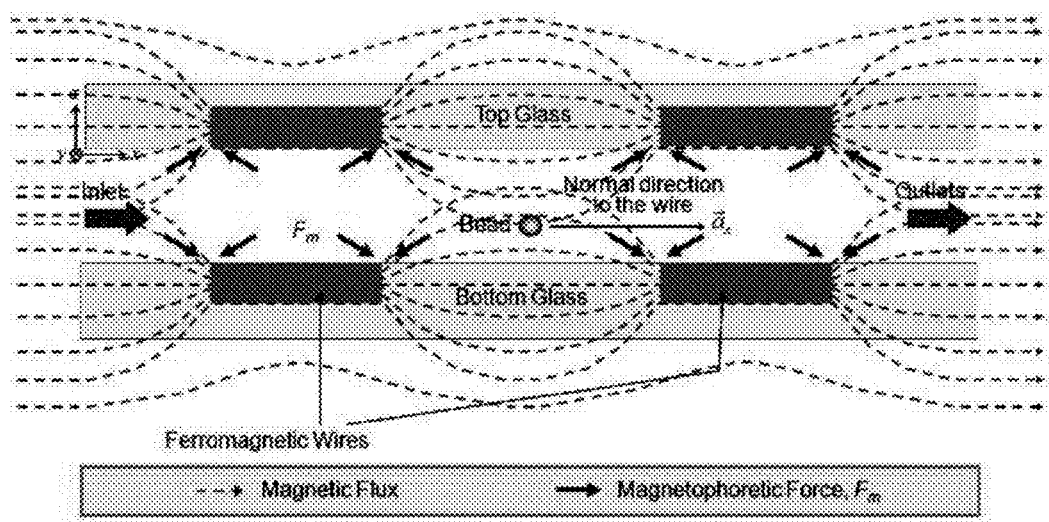
FIG. 11 is a mimetic drawing showing the apparatus for separating fine particles using magnetophoresis, which also contains the fine structure of a magnetic material in the upper substrate, according to another embodiment of the present invention.
Figure 12:
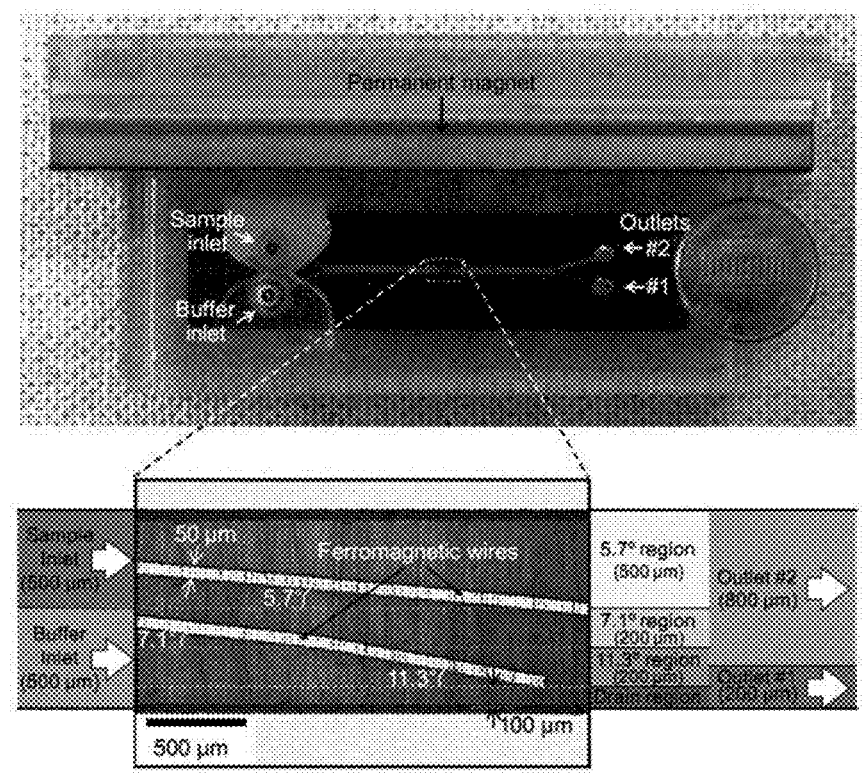
FIG. 12 is a drawing showing the apparatus for separating fine particles using magnetophoresis manufactured according to one embodiment of the present invention.

Then, SU-8 was formed on an upper glass substrate as a microfluidic channel pattern, an upper glass substrate was manufactured by making a sample inlet by using Nitrile rubber O-rings (size 001-1/2, McMaster-Carr, IL, USA), and the manufactured lower glass substrate and a UV adhesive (1187-M, DYMAX Co., Torrington, Conn.) were joined together so as to finally complete an apparatus for separating fine particles using magnetic flux as shown in FIG. 12.

<Example 1> RNA Separation

<Example 1-1> RNA Separation From Blood

As magnetic particles, 2.8 μm diameter magnetic beads (Dynabeads Oligo (dT)25) were used. Human blood 50 μl was collected from a finger, and RNA lysis buffer 175 μl A was mixed with the magnetic particles to manufacture a sample comprising RNA combined with the magnetic particles. The sample prepared above was injected into the sample inlet of the apparatus for separating fine particles manufactured in Example 1.

Figure 13:
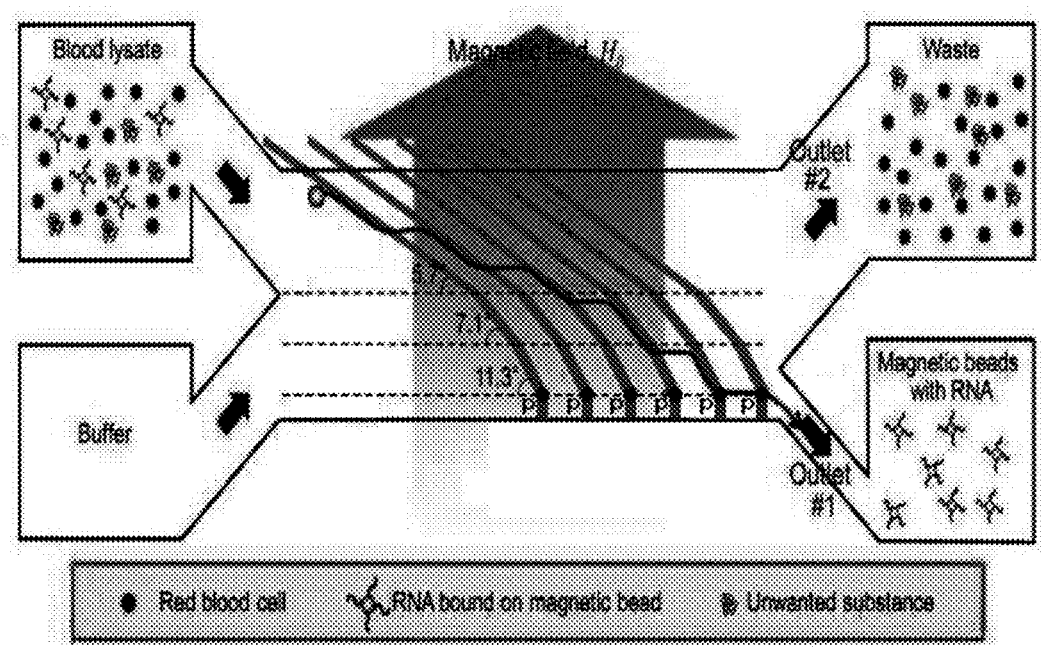
FIG. 13 is a drawing mimetically showing a process for separating the RNA combined with the magnetic particles by using the apparatus for separating the fine particles combined with the magnetic particles using magnetophoresis manufactured according to one embodiment of the present invention.

A process for separating RNA in the fine particle separating apparatus comprising a plurality of fine structures of a magnetic material, when the angle of inclination to the fluidic flow was changed at the same point with the same angle, was mimetically illustrated in FIG. 13.

Figure 14:
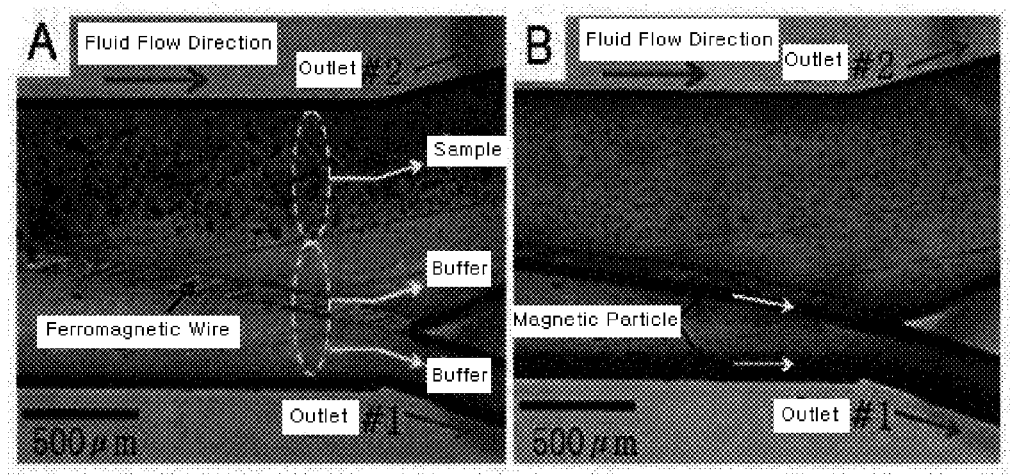
FIG. 14 is images showing that the RNA combined with the magnetic particles flow along the channel when an external magnetic field was applied or not applied to the apparatus for separating the fine particles combined with the magnetic particles using magnetophoresis manufactured according to one embodiment of the present invention.

Images of white blood cell-dissolved blood and the magnetic particles flowing along the channel when an external magnetic field was applied or not applied to the particle separating apparatus manufactured in Preparation Example 1 were illustrated in FIG. 14A and FIG. 14B, respectively. When the external magnetic field was applied, it could be confirmed that the blood and the RNA combined with the magnetic particles are apparently separated and collected.

<Example 1-2> Measuring Separation Efficiency According to Sample Flow Rate

Figure 15:
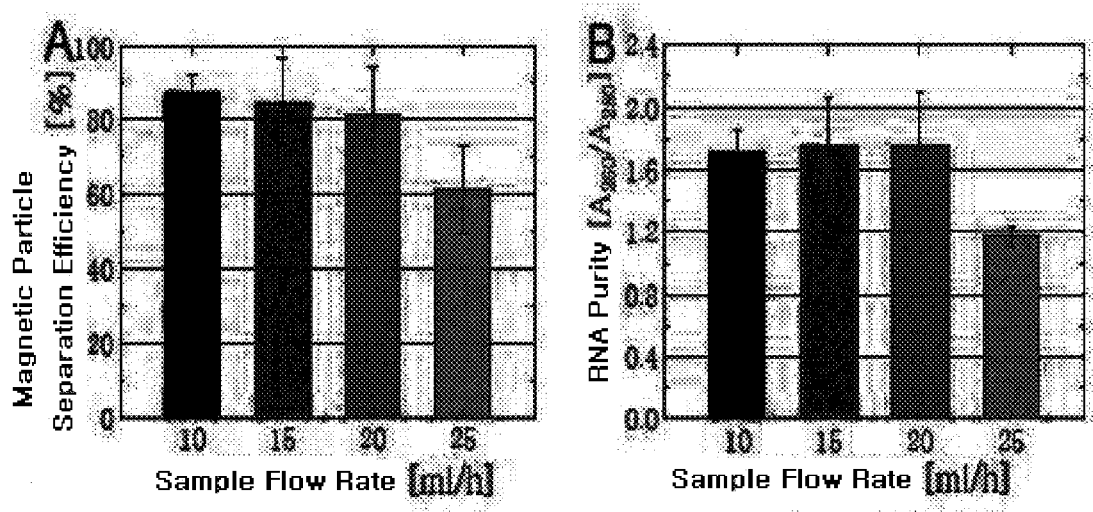
FIG. 15 is a drawing showing the results of the efficiency separating the RNA combined with the magnetic particles and the purity of the RNA according to change the sample flow rate when separating the RNA combined with the magnetic particles by using the apparatus for separating the fine particles combined with the magnetic particles using magnetophoresis manufactured according to one embodiment of the present invention.

The procedure of Example 1 was repeated, and efficiency for separating the RNA combined with the magnetic particles and purity of the separated RNA when sample flow rate was changed to 10, 15, 20 and 25 ml/h, respectively, were measured, and the results were shown in FIG. 15a and FIG. 15b.

As shown in FIG. 15a and FIG. 15b, according to increase of the sample flow rate, the efficiency for separation was decreased. Accordingly, it could be found that: the efficiency for separation can be controlled by changing the sample flow rate according to the fine particles to be separated; and in the case of the blood, it is preferred that the sample flow rate may be 15 to 20 ml/h in terms of the efficiency and the speed for separation in order to separate RNA.

<Test Example 1> Performing RT-PCR Using Separated RNA

Whether the RNA extract according to the present invention can be used for performing RT-PCR or not was checked by performing RT-PCR for detecting a human β actin (219 bp) using the RNA separated in Example 1.

Figure 16:
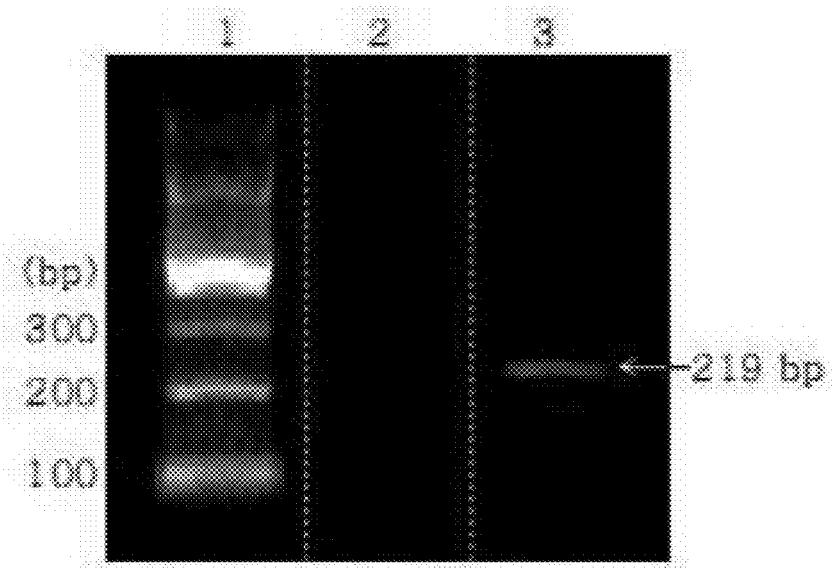
FIG. 16 is a drawing showing the result of RT-PCR for detecting human β actin (219 bp) from the RNA extract according to one embodiment of the present invention.

After performing the RT-PCR, the result of the gel electrophoresis shown in FIG. 16 was obtained, and accordingly, it can be found that the RNA separated according to the RNA extraction method of the present invention can be used for the RT-PCR.

<Preparation Example 2> Manufacturing Apparatus for Separating Fine Particles Combined with Magnetic Particles Using Magnetophoresis In this Example, two ferromagnetic wires were formed to be contained in the lower glass substrate of the microfluidic channel for separation part. The procedure of Preparation Example 1 was repeated to manufacture the apparatus for separating the fine particles combined with the magnetic particles by magnetophoresis except that: the width of the wire was 50 μm, the both of the two wires were contained with the angle of inclination of 5.7° to the direction of the sample flow, and it is patterned to have the angle of inclination of 90° near the outlet. The fine structure of a magnetic material in the manufactured separation apparatus and the state of separating the CTC using the same were illustrated in FIG. 17.

<Example 2> Separation of Circulating Tumor Cells (CTC)

Example 2-1

Blood sample was collected from a breast cancer patient and a lung cancer patient, and the circulating tumor cells in the sample were combined with magnetic nanoparticles by mixing with the magnetic nanoparticles labeled with anti- EpCAM antibody against an epithelial cell adhesion molecule. As the magnetic particles, magnetic nanobeads (STEMCELL Technologies), which has the diameter of several tens nm and is coated with the anti-EpCAM antibody.

Figure 17:
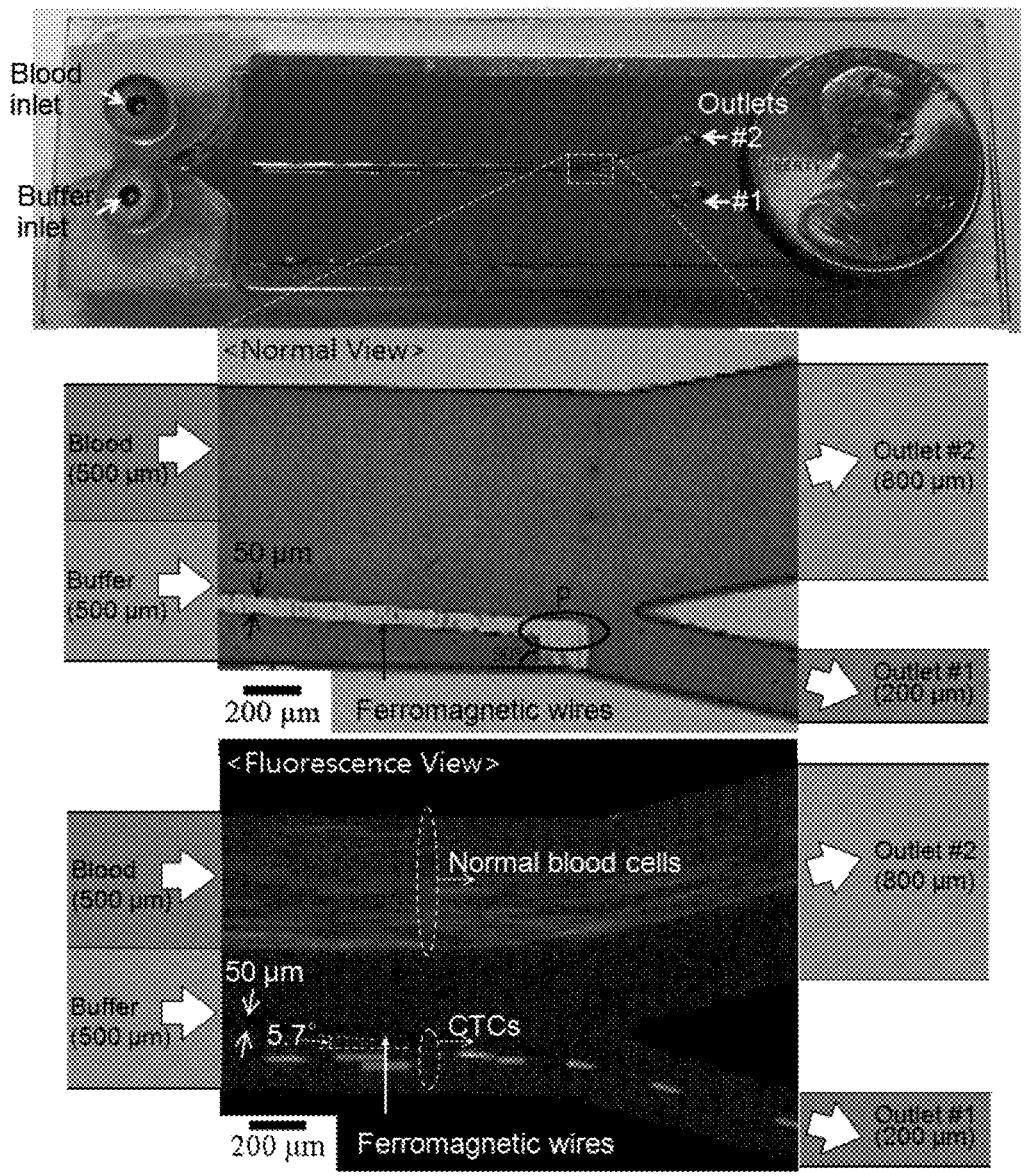
FIG. 17 is an image of the apparatus for separating fine particles using magnetophoresis manufactured according to another embodiment of the present invention, and an image showing that the circulating tumor cells combined with the magnetic particles flow along the channel of the separation apparatus when separating the circulating tumor cells by using the separating apparatus.

The blood sample comprising the circulating tumor cells combined with the magnetic particles as prepared above was injected into the apparatus for separating fine particles manufactured in Preparation Example 2. An enlarged image, showing that the circulating tumor cells combined with the magnetic particles flow along the channel of the apparatus for separating fine particles manufactured in Preparation Example 2 when applying the external magnetic field source to the fine structure of a magnetic consisting of the ferromagnetic nickel wire, was illustrated in FIG. 17. As shown in FIG. 17, it could be confirmed that the circulating tumor cells combined with the magnetic particles were separated while moving to the lateral direction when the external magnetic field was applied.

<Example 2-2> Measuring Separation Efficiency According to Sample Flow Rate

Figure 18:
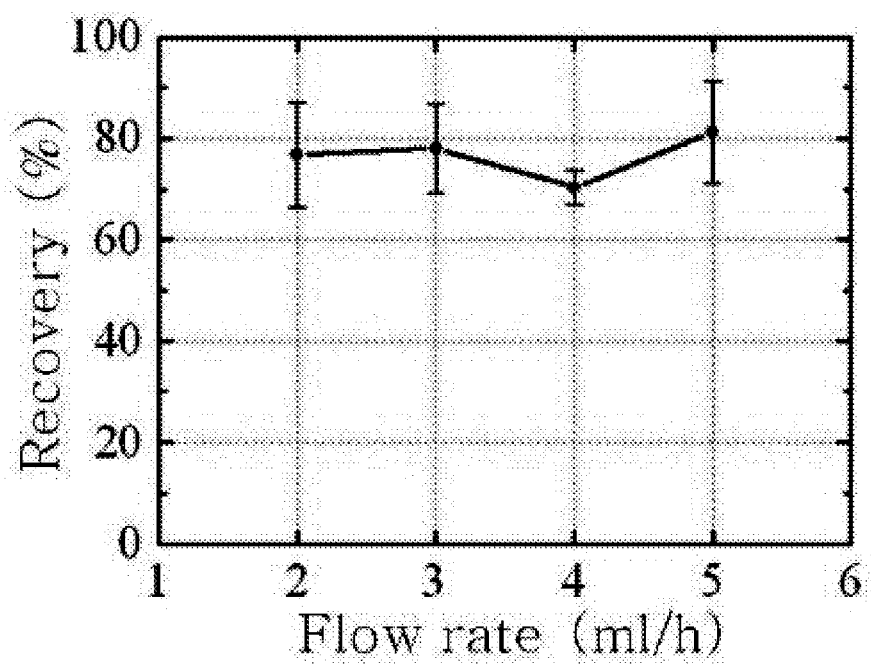
FIG. 18 is a drawing showing the result of measuring the separation efficiency of the circulating tumor cells combined with the magnetic particles when changing the flow rate of the sample.

The procedure of Example 2-1 was repeated, and the separation efficiency of the circulating tumor cells combined with the magnetic particles, and the purity of the separated circulating tumor cells were measured when changing the sample flow rate to 2, 3, 4 and 5 ml/h, respectively, and the result was shown in FIG. 18.

As shown in FIG. 18, the separation efficiency of circulating tumor cells combined with the magnetic particles was 78.7%, and it could be found that the separation efficiency for the circulating tumor cells was not changed by the flow rate in the flow rate range of 2 to 5 ml/h.

Figure 19:
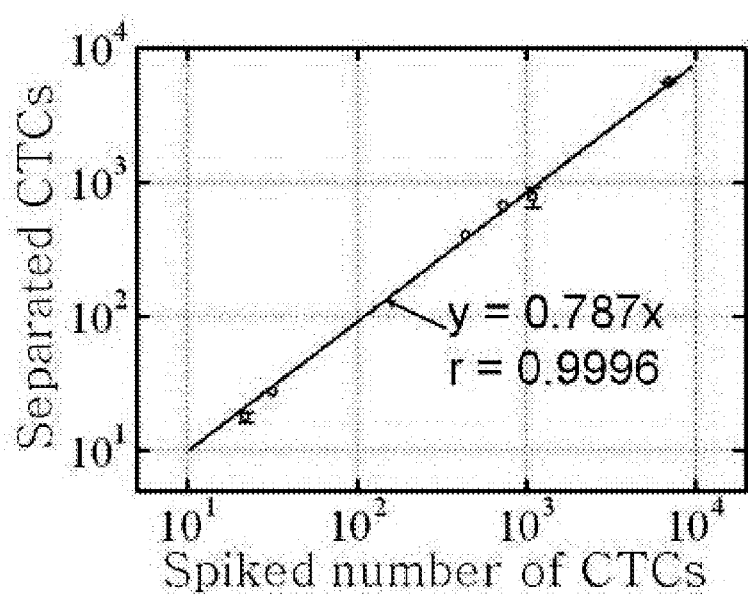
FIG. 19 is a drawing showing the result of measuring the number of the circulating tumor cells separated by using the apparatus for separating fine particles according to one embodiment of the present invention while changing the number of the circulating tumor cells spiked in the sample.

<Example 2-3> Measuring Separation Efficiency According to Content of Circulating Tumor Cells in Sample The procedure of Example 2-1 was repeated, and the number of the circulating tumor cells separated by the apparatus for separating fine particles manufactured in Preparation Example 2 while changing the number of the circulating tumor cells spiked in the sample to 10, $10^2$, $10^3$ and $10^4$, and the result was shown in FIG. 19. As shown in FIG. 19, it could be found that the number of the spiked circulating tumor cells and the number of the separated circulating tumor cells are reciprocally proportional, and the separation efficiency of the circulating tumor cells was very high of 79%.

Figure 20:
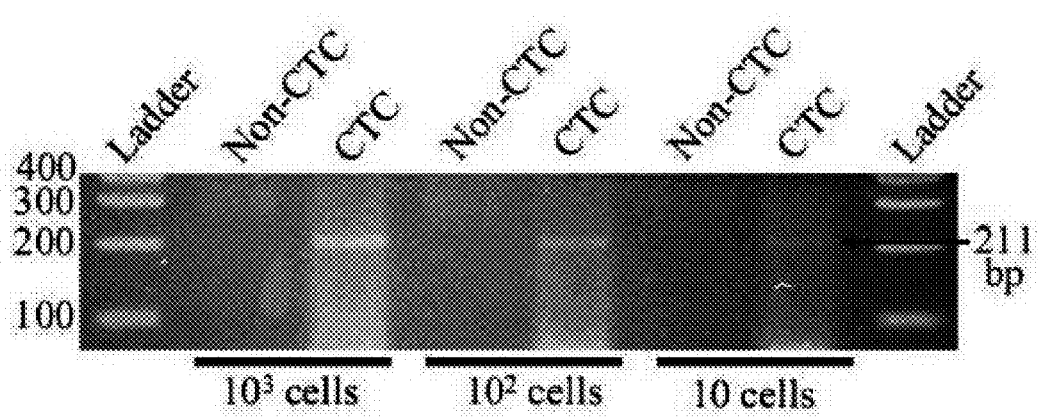
FIG. 20 is a drawing showing the result of performing RT-PCR to the circulating tumor cells separated by using the apparatus for separating fine particles according to one embodiment of the present invention.

<Example 2-4> Performing RT-PCR According to Amount of Spike of Circulating Tumor Cells in Sample To each sample containing the number of the spiked circulating tumor cells of 10, $10^2$ and $10^3$, respectively, RT-PCR was performed to detect the circulating tumor cells separated in Example 2-3, and the result was shown in FIG. 20.

As the result of RT-PCR shown in FIG. 20, it could be confirmed that the cells were separated by PCR even when the number of the spiked circulating tumor cells is very small of 10.

<Example 2-5> Separation of CTC Cells from Cancer Patient

Figure 21:
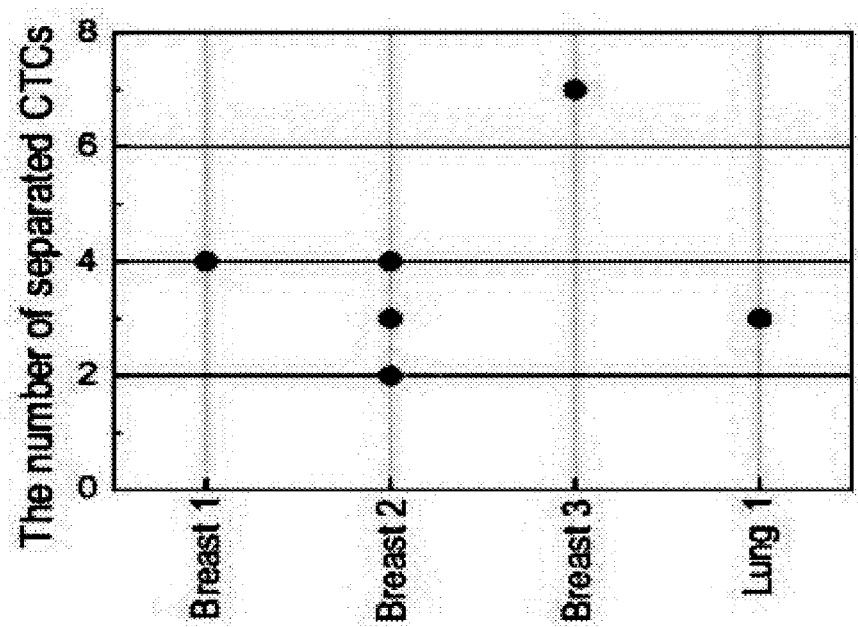
FIG. 21 is a drawing showing the result of separating the circulating tumor cells from patients of breast cancer and lung cancer by using the apparatus for separating fine particles according to one embodiment of the present invention.

The circulating tumor cells were separated from samples of three breast cancer patients and one lung cancer patient by the apparatus separating fine particles manufactured in Preparation Example 2, and the result was shown in FIG. 21. It could be confirmed that the circulating tumor cells were completely separated in FIG. 21.

INDUSTRIAL APPLICABILITY

The apparatus for separating the fine particles using magnetophoresis of the present invention has effects of: improving the magnetic force applied to the magnetic particles by comprising the fine structure of a magnetic material on the lower glass substrate by a molding process; and improving the efficiency for separating the fine particles combined with the magnetic particles and reducing the separation time by controlling the moving direction of the magnetic particles by patterning the fine structure of a magnetic material to have a certain angle of inclination of the direction of sample flow.

While the invention has been described with respect to the above specific embodiments, it should be recognized that various modifications and changes may be made and also fall within the scope of the invention as defined by the claims that follow.

What is claimed is:
1. An apparatus for separating fine particles using magnetophoresis comprising:
an upper substrate;
a lower substrate comprising a fine structure of a magnetic material;
a microfluidic channel, which is formed between the upper substrate and the lower substrate, and where a sample comprising fine particles passes in a sample flow direction, the sample comprising magnetic fine particles; and
an external magnetic field source generating a magnetic field around the fine structure of the magnetic material;
the microfluidic channel is divided into a microfluidic channel domain for injection, a microfluidic channel domain for separation, and a microfluidic channel domain for discharge;
wherein the fine structure of the magnetic material is plurality of linear structures, and is patterned and contained in the lower substrate by molding,
wherein the sample flow direction has an angle θ and each linear structure has angles of inclination relative to the sample flow direction, $\theta_1$, $\theta_2$, $\theta_3$ . . . $\theta_n$, in order respectively, in the direction from the microfluidic channel domain for injection to the microfluidic channel domain for discharge, the angles of inclination relative to the sample flow direction, $\theta_1$, $\theta_2$, $\theta_3$ . . . $\theta_n$, satisfying the following relation expression:

$\theta_1 \leq \theta_2 \leq \theta_3 \leq \ldots \theta_n (3 \leq n)$;

wherein the point (P) where the angle of inclination is changed from $\theta_{n-1}$ to $\theta_n$ is located in a horizontally extended part of the microfluidic channel domain for discharge,
wherein the angle $\theta_n$ is 90°,
wherein the fine structure of the magnetic material is patterned to make both sides of the microfluidic channel have symmetry based on the center line of the microfluidic channel domain for separation.
2. The apparatus for separating fine particles using magnetophoresis according to claim 1, wherein the microfluidic channel is divided into:

the microfluidic channel domain for injection comprising a sample inlet and a buffer inlet, where the sample comprising fine particles and a buffer are injected;

the microfluidic channel domain for separation, where the sample comprising fine particles is separated by magnetophoresis while passing through into a separated sample comprising magnetic fine particles and the rest of the separated sample; and the microfluidic channel domain for discharge comprising a plurality of outlets, where the separated sample comprising magnetic fine particles and the rest of the separated sample are separately discharged.

3. The apparatus for separating fine particles using magnetophoresis according to claim 2, wherein the microfluidic channel domain for discharge comprises an outlet for the separated sample comprising magnetic fine particles, and an outlet for the rest of the separated sample.

4. The apparatus for separating fine particles using magnetophoresis according to claim 2, wherein the microfluidic channel domain for injection comprises the buffer inlet, and the sample inlet, which is a plurality of sample inlets symmetrically formed on both sides of the buffer inlet.

5. The apparatus for separating fine particles using magnetophoresis according to claim 2, wherein the microfluidic channel domain for injection comprises the sample inlet, and the buffer inlet, which is a plurality of buffer inlets symmetrically formed on both sides of the sample inlet.

6. The apparatus for separating fine particles using magnetophoresis according to claim 1, wherein the fine structure of the magnetic material comprises a nickel-iron alloy or a nickel-iron-cobalt alloy.

7. The apparatus for separating fine particles using magnetophoresis according to claim 6, wherein the fine structure of the magnetic material is any one of permalloy (Fe 50%, Ni 50%), moly permalloy (Ni 81%, Fe 17%, Mo 2%) or superalloy (Co 52%, Fe 26%, Ni 22%).

8. The apparatus for separating fine particles using magnetophoresis according to claim 1, wherein in the apparatus for separating fine particles using magnetophoresis, the angles of inclination relative to the sample flow direction, $\theta_1, \theta_2, \theta_3 \ldots \theta_n$ of each linear structure of the plurality of linear structures, the thickness of the fine structure of the magnetic material, gap between adjacent linear structures of the plurality of linear structures of the fine structure of the magnetic material, the number of linear structures of the plurality of linear structures to be installed, the size of the external magnetic field source and the fluid flow rate in the microfluidic channel are changed according to the sample comprising fine particles to be separated.

9. The apparatus for separating fine particles using magnetophoresis according to claim 1, wherein the upper substrate comprises a patterned fine structure of a magnetic material, patterned in the same shape as the fine structure of the magnetic material of the lower substrate.

10. A method for separating fine particles using magnetophoresis and using the apparatus of claim 1 for separating fine particles using magnetophoresis comprising:

a first step of injecting the sample comprising fine particles, the sample comprising magnetic fine particles into a sample inlet of the microfluidic channel domain for injection;

a second step of injecting a buffer into a buffer inlet of the microfluidic channel domain of infection;

a third step of separating the sample comprising magnetic fine particles from the rest of the sample comprising fine particles, wherein an external magnetic field source is generated, thereby a magnetic force is generated around the fine structure of the magnetic material, and the sample comprising magnetic fine particles is separated from the rest of the sample comprising fine particles by the magnetic force generated around the fine structure of the magnetic material while the rest of the sample comprising fine particles is passing through the microfluidic channel domain for separation; and a fourth step of collecting separately, the rest of the sample comprising fine particles and the sample comprising fine magnetic particles separated in the third step at the microfluidic channel domain for discharge.

\* \* \* \* \*